United States Patent
Šarek et al.

(10) Patent No.: US 8,680,251 B2
(45) Date of Patent: Mar. 25, 2014

(54) TRITERPENOID 2-DEOXY GLYCOSIDES, METHOD OF PREPARATION THEREOF AND USE THEREOF AS MEDICAMENTS

(75) Inventors: Jan Šarek, Horní Měcholupy (CZ); Pavla Spáčilová, Ostrava (CZ); Marian Hajduch, Moravský Beroun (CZ)

(73) Assignee: Univerzita Palackeho V Olomouci, Olomouc (CZ)

( * ) Notice: Subject to any disclaimer, the term of this patent is extended or adjusted under 35 U.S.C. 154(b) by 211 days.

(21) Appl. No.: 13/128,818

(22) PCT Filed: Nov. 6, 2009

(86) PCT No.: PCT/CZ2009/000132
§ 371 (c)(1),
(2), (4) Date: May 11, 2011

(87) PCT Pub. No.: WO2010/054606
PCT Pub. Date: May 20, 2010

(65) Prior Publication Data
US 2011/0218167 A1    Sep. 8, 2011

(30) Foreign Application Priority Data
Nov. 13, 2008  (CZ) .................. PV 2008-723

(51) Int. Cl.
*C07H 15/04*   (2006.01)
*A61K 31/19*   (2006.01)

(52) U.S. Cl.
USPC ........... 536/4.1; 536/18.5; 514/25; 514/26; 514/253.08; 514/569

(58) Field of Classification Search
CPC ........................................... C07H 15/04
USPC ............ 536/4.1, 5, 18.5; 514/25, 26, 253.08, 514/569
See application file for complete search history.

(56) References Cited

U.S. PATENT DOCUMENTS 6,369,109 B1 *  4/2002  Debatin et al. .............. 514/569

* cited by examiner

*Primary Examiner* — Patrick Lewis
*Assistant Examiner* — Everett White
(74) *Attorney, Agent, or Firm* — Notaro, Michalos & Zaccaria P.C.

(57) ABSTRACT

The invention describes novel triterpenoid 2-deoxy glycosides of general formula I, wherein at least one of the substituents $X^1$ and $R^2$ contains a 2-deoxy glycosidic group, method of preparation thereof, their cytotoxic activity and a pharmaceutical formulation containing these compounds.

5 Claims, 1 Drawing Sheet

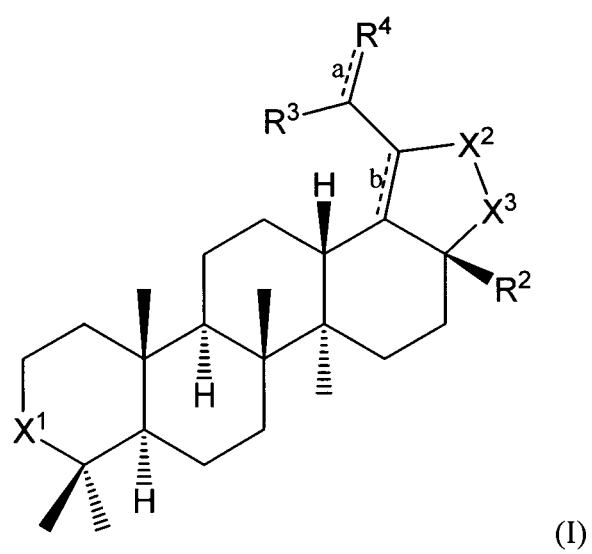
(I)

TRITERPENOID 2-DEOXY GLYCOSIDES, METHOD OF PREPARATION THEREOF AND USE THEREOF AS MEDICAMENTS

FIELD OF THE ART

The invention relates to triterpenoid 2-deoxy glycosides, method of preparation thereof and use thereof as medicaments.

BACKGROUND ART

Pentacyclic and tetracyclic terpenoids form a part of a group of naturally occurring substances (isoprenoids) that show a large range of biological activities (Dzubak, P.; Hajduch, M.; Vydra, D.; Hustova, A.; Kvasnica, M.; Biedermann, D.; Markova, L.; Urban, M.; Sarek, J. Nat. Prod. Rep. 2006, 23, 394). Among the substances showing an excellent in vitro cytotoxic activity belongs, e.g., betulinic acid. The cytotoxic activity of some triterpenoid derivatives is mentioned in patent literature (Hajduch M., Sarek J.: Triterpenoid derivates. PCT Int. Patent Appl. WO0190136, 23 May 2001; Hajduch M., Sarek J.: Triterpenoid derivates. PCT Int. Patent Appl. WO0190046, 23 May 2001; Hajduch M., Sarek J.: Triterpenoid derivates. PCT Int. Patent Appl. WO0190096, 23 May 2001).

So far, only few terpenic 2-deoxy glycosides were synthesized. First, they were prepared by reaction with NIS (N-bromosuccinimide), wherein the formed 2-deoxy-2-iodo glycosides yielded acetylated 2-deoxy glycosides by reaction with 10% Pd/C or reacted with methanolic KOH solution, yielding free 2-deoxy glycosides (Flekheter, O. B.; Baltina, L. A.; Vasileva, E. V.; Tolstikov, G. A.: Russ. Chem. Bull. 1996, 45, 2993).

Later, triterpenic 2-deoxy glycosides were prepared using katex in H$^+$ cycle and lithium bromide in a mixture of acetonitrile and dichloromethane (Flekheter, O. B.; Baltina, L. A.; Tolstikov, G. A.: J. Nat. Prod. 2000, 63, 992). The reaction is quenched by triethylamine and followed by deacetylation by methanolic KOH. When glycals are used, α-anomers of 2-deoxy glycosides are formed.

Several 2-deoxy glycosides of naturally occurring and synthetic oleanane, lupane and ursane hydroxy derivatives were already prepared by these two methods; among oleanane derivatives were, e.g., 2-deoxy glycosides of glycyrrhetic acid derivatives (Flekheter, O. B.; Baltina, L. A.; Vasileva, E. V.; Tolstikov, G. A.: Russ. Chem. Bull. 1996, 45, 2993), allobetuline 2-deoxy glucoside (Baltina, L. A.; Flekheter, O. B.; Vasiljieva, E. V.: Mendeleev Commun. 1996, 6, 63), among lupane derivatives betulin-28-acetate-2-deoxy-L-arabinoside may be listed (Flekheter, O. B.; Baltina, L. A.; Tolstikov, G. A.: J. Nat. Prod. 2000, 63, 992). Also, the preparation of acetylated cholesterol 2-deoxy-glucoside was published (Bollit, V.; Miostovski, C.; Lee, S. G.; Falck, J. R.: J. Org. Chem. 1990, 55, 5812).

The patent application Sarek, J. et al.: WO 2008/037226 teaches the preparation of soluble formulation containing inclusion complexes of cyclodextrins and triterpenoid derivatives, inter alia several 2-deoxy glycosides showing a better bioavailability, but does not describe any activity of such compounds.

The present invention provides novel triterpenoid 2-deoxy glucosides having cytotoxic activity.

BRIEF DESCRIPTION OF THE DRAWINGS

In the drawings:
FIG. 1 is general formula I for a triterpenoid 2-deoxy glycoside of the invention.

DISCLOSURE OF THE INVENTION

Object of the invention are triterpenoid 2-deoxy glycosides of general formula I

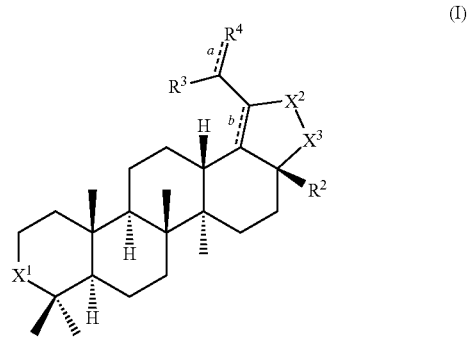

(I)

wherein:
each of "a" and "b" is a double (d) or a single (s) bond;
$R^2$ is selected from the group comprising COOH, COOCH$_2$C$_6$H$_5$, COO(CH$_2$)$_n$CH$_3$, wherein n=0-10 (preferably 0 or 1), and CH$_2$OR$^{2a}$;
$R^3$ is CH$_3$ or CHO;
$R^4$ is CH$_3$ or CH$_2$;
$X^1$ is CHOR$^1$ or C═O;
$X^2$, $X^3$ are independently CH$_2$ or C═O;
$R^1$ is selected from the group comprising acetyl (Ac), 2-deoxy-α-D-galactopyranosyl (2-deoxyGal), 3,4,6-tri-O-acetyl-2-deoxy-α-D-galactopyranosyl (2-deoxyAc$_3$Gal), 2-deoxy-α-D-glucopyranosyl (2-deoxyGlc), 3,4,6-tri-O-acetyl-2-deoxy-α-D-glucopyranosyl (2-deoxyAc$_3$Glc), 4,6-di-O-acetyl-3-brom-2,3-dideoxy-α-D-glucopyranosyl (2-deoxyBrAc$_2$Glc), 4-(2',3',4',6'-tetra-O-acetyl-β-D-galactopyranosyl)-3,6-di-O-acetyl-2-deoxy-α-D-glucopyranosyl (2-deoxyAc$_6$Lac), 4-(β-D-galactopyranosyl)-2-deoxy-α-D-glucopyranosyl (2-deoxyLac), 4-(2',3',4',6'-tetra-O-acetyl-α-D-glucopyranosyl)-3,6-di-O-acetyl-2-deoxy-α-D-glucopyranosyl (2-deoxyAc$_6$Mal), 4-(α-D-glucopyranosyl)-2-deoxy-α-D-glucopyranosyl (2-deoxyMal), 4-(2',3',4',6'-tetra-O-acetyl-β-D-galactopyranosyl)-6-O-acetyl-2,3-dideoxy-α-D-erythro-hex-2-enopyranosyl (FerrierAc$_5$Lac), 4-(β-D-galactopyranosyl)-2,3-dideoxy-α-D-erythro-hex-2-enopyranosyl (FerrierLac), 4-(2',3',4',6'-tetra-O-acetyl-α-D-glucopyranosyl)-6-O-acetyl-2,3-dideoxy-α-D-erythro-hex-2-enopyranosyl (FerrierAc$_5$Mal), 4-(α-D-glucopyranosyl)-2,3-dideoxy-α-D-erythro-hex-2-enopyranosyl (FerrierMal), 3,4-di-O-acetyl-2-deoxy-α-L-rhamnosyl (2-deoxyAc$_2$Rha), 2-deoxy-α-L-rhamnosyl (2-deoxyRha), 4-O-acetyl-2,3-dideoxy-3-brom-α-L-rhamnosyl (2-deoxyAcBrRha), 4-O-acetyl-2,3,6-trideoxy-α-L-erythro-hex-2-enopyranosyl (FerrierAcRha), 2,3,6-trideoxy-α-L-erythro-hex-2-enopyranosyl (FerrierRha) and hydrogen;
$R^{2a}$ is selected from the group comprising 2-deoxy-α-D-galactopyranosyl (2-deoxyGal), 3,4,6-tri-O-acetyl-2-deoxy-α-D-galactopyranosyl (2-deoxyAc$_3$Gal), 2-deoxy-α-D-glucopyranosyl (2-deoxyGlc), 3,4,6-tri-O-acetyl-2-deoxy-α-D-glucopyranosyl (2-deoxyAc$_3$Glc), 4,6-di-O-acetyl-3-brom- 2,3-dideoxy-α-D-glucopyranosyl (2-deoxyBrAc$_2$Glc), 4-(2', 3',4',6'-tetra-O-acetyl-β-D-galactopyranosyl)-3,6-di-O-acetyl-2-deoxy-α-D-glucopyranosyl (2-deoxyAc$_6$Lac), 4-(β-D-galactopyranosyl)-2-deoxy-α-D-glucopyranosyl (2-deoxyLac), 4-(2',3',4',6'-tetra-O-acetyl-α-D-glucopyranosyl)-3,6-di-O-acetyl-2-deoxy-α-D-glucopyranosyl (2-deoxyAc$_6$Mal), 4-(α-D-glucopyranosyl)-2-deoxy-α-D-glucopyranosyl (2-deoxyMal), 4-(2',3',4',6'-tetra-O-acetyl-(β-D-galactopyranosyl)-6-O-acetyl-2,3-dideoxy-α-D-erythro-hex-2-enopyranosyl (FerrierAc$_5$Lac), 4-(β-D-galactopyranosyl)-2,3-dideoxy-α-D-erythro-hex-2-enopyranosyl (FerrierLac), 4-(2',3',4',6'-tetra-O-acetyl-α-D-glucopyranosyl)-6-O-acetyl-2,3-dideoxy-α-D-erythro-hex-2-enopyranosyl (FerrierAc$_5$Mal), 4-(α-D-glucopyranosyl)-2,3-dideoxy-α-D-erythro-hex-2-enopyranosyl (FerrierMal), 3,4-di-O-acetyl-2-deoxy-α-L-rhamnosyl (2-deoxyAc$_2$Rha), 2-deoxy-α-L-rhamnosyl (2-deoxyRha), 4-O-acetyl-2,3-dideoxy-3-brom-α-L-rhamnosyl (2-deoxyAcBrRha), 4-O-acetyl-2,3,6-trideoxy-α-L-erythro-hex-2-enopyranosyl (FerrierAcRha), 2,3,6-trideoxy-α-L-erythro-hex-2-enopyranosyl (FerrierRha) and hydrogen;

provided that:
when "a" is a single bond (s), "b" is a double bond (d), and when "b" is a single bond (s), "a" is a double bond (d);
when "a" is a single bond, R$^4$ is CH$_3$, and when "a" is a double bond, R$^4$ is CH$_2$;
when X$^2$ is C=O and X$^3$ is CH$_2$, "a" is a single bond (s) and "b" is a double bond (d);
when X$^2$ is C=O and X$^3$ is C=O, "a" is a single bond (s) and "b" is a double bond (d);
at least one of X$^1$ and R$^2$ comprises 2-deoxy glycosyl
for use as medicaments.

The limitation "at least one of X$^1$ and R$^2$ comprises 2-deoxy glycosyl" shall be interpreted as meaning that when X$^1$ is C=O, R$^2$ is CH$_2$OR$^{2a}$, wherein R$^{2a}$ is 2-deoxy glycosyl, and when R$^2$ has any other meaning than CH$_2$OR$^{2a}$, wherein R$^{2a}$ is 2-deoxy glycosyl, X$^1$ must be CHOR$^1$, wherein R$^1$ is 2-deoxy glycosyl.

Herein, by the term "2-deoxy glycosyl" is meant a group selected from 2-deoxyGal, 2-deoxyAc$_3$Gal, 2-deoxyGlc, 2-deoxyAc$_3$Glc, 2-deoxyBrAc$_2$Glc, 2-deoxyAc$_6$Lac, 2-deoxyLac, 2-deoxyAc$_6$Mal, 2-deoxyMal, FerrierAc$_5$Lac, FerrierLac, FerrierAc$_5$Mal, FerrierMal, 2-deoxyAc$_2$Rha, 2-deoxyRha, 2-deoxyAcBrRha, FerrierAcRha, FerrierRha.

It is especially advantageous when X$^2$ and X$^3$ are not both CH$_2$ at the same time.

Object of the invention are further the compounds of general formula I for use as medicaments, particularly in the treatment of tumor diseases and diseases with pathological proliferation, preferably leukemic diseases, lung carcinomas, breast carcinomas, colorectal carcinomas and glioblastomas.

Object of the invention is further use of the compounds of general formula I in the manufacture of a medicament for the treatment of tumor diseases and diseases with pathological proliferation, preferably leukemic diseases, lung carcinomas, breast carcinomas, colorectal carcinomas and glioblastomas.

Another object of the invention is a pharmaceutical composition, destined for the treatment of tumor diseases and diseases with pathological proliferation, preferably leukemic diseases, lung carcinomas, breast carcinomas, colorectal carcinomas and glioblastomas, which contains at least one compound of general formula I and pharmaceutically acceptable carrier.

The compounds of general formula I may be used in a method of treatment of a mammal suffering from a disease selected from the group comprising tumor diseases and diseases with pathological proliferation by administering a compound of general formula I to said mammal.

Object of the present invention is further a method of preparation of the compounds of general formula I, comprising the steps of:

a) reaction of triterpenic hydroxy derivative of general formula II

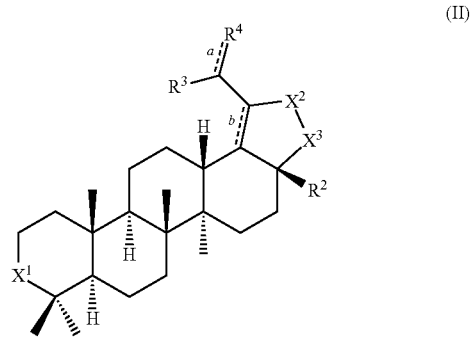

wherein:
each of "a" and "b" is a double (d) or a single (s) bond;
R$^2$ is COO(CH$_2$)$_n$CH$_3$, wherein n=0-10 (preferably 0 or 1), COOCH$_2$C$_6$H$_5$, COOH or CH$_2$OH;
R$^3$ is CH$_3$ or CHO;
R$^4$ is CH$_3$ or CH$_2$;
X$^1$ is CHOR$^1$ or C=O;
X$^2$, X$^3$ are independently CH$_2$ or C=O;
R$^1$ is acetyl (Ac) or hydrogen;
provided that:
when "a" is a single bond (s), "b" is a double bond (d), and when "b" is a single bond (s), "a" is a double bond (d);
when "a" is a single bond, R$^4$ is CH$_3$, and when "a" is a double bond, R$^4$ is CH$_2$.
when X$^2$ is C=O and X$^3$ is CH$_2$, "a" is a single bond (s) and "b" is a double bond (d);
when X$^2$ is C=O and X$^3$ is C=O, "a" is a single bond (s) and "b" is a double bond (d);
when R$^2$ is not CH$_2$OH, X$^1$ is CHOR$^1$ and R$^1$ is hydrogen,
with acetylated glycal (glucal, galactal, rhamnal, lactal, maltal) in dry nitrile solvent, preferably acetonitrile or benzonitrile, in the presence of katex in H$^+$ cycle, halogenide, preferably lithium bromide, and molecular sieve, preferably molecular sieve 4 A, yielding acetylated triterpenoid 2-deoxy glycoside;

b) the acetylated triterpenoid 2-deoxy glycoside formed in step a) is optionally deacetylated by Zemplén deacetylation by treatment with sodium alcoholate in dry alcohol, preferably with sodium methanolate in methanol or in a mixture of methanol and ethanol.

It is an advantage of the above described process that only α-anomer of the 2-deoxy glycoside is yielded. The reaction is carried out under mild conditions and also working-up of the reaction mixture is facile.

Another object of the invention are triterpenoid 2-deoxy glycosides of general formula Ia

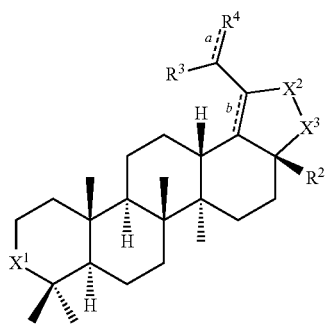

wherein:
each of "a" and "b" is a double (d) or a single (s) bond;
$R^2$ is selected from the group comprising COOH, $COOCH_2C_6H_5$, $COO(CH_2)_nCH_3$, wherein n=0-10 (preferably 0 or 1), and $CH_2OR^{2a}$;
$R^3$ is $CH_3$ or CHO;
$R^4$ is $CH_3$ or $CH_2$;
$X^1$ is $CHOR^1$ or C=O;
$X^2$, $X^3$ are independently $CH_2$ or C=O;
$R^1$ is selected from the group comprising acetyl (Ac), 2-deoxy-α-D-galactopyranosyl (2-deoxyGal), 3,4,6-tri-O-acetyl-2-deoxy-α-D-galactopyranosyl (2-deoxyAc₃Gal), 2-deoxy-α-D-glucopyranosyl (2-deoxyGlc), 3,4,6-tri-O-acetyl-2-deoxy-α-D-glucopyranosyl (2-deoxyAc₃Glc), 4,6-di-O-acetyl-3-brom-2,3-dideoxy-α-D-glucopyranosyl (2-deoxyBrAc₂Glc), 4-(2',3',4',6'-tetra-O-acetyl-β-D-galactopyranosyl)-3,6-di-O-acetyl-2-deoxy-α-D-glucopyranosyl (2-deoxyAc₆Lac), 4-(β-D-galactopyranosyl)-2-deoxy-α-D-glucopyranosyl (2-deoxyLac), 4-(2',3',4',6'-tetra-O-acetyl-α-D-glucopyranosyl)-3,6-di-O-acetyl-2-deoxy-α-D-glucopyranosyl (2-deoxyAc₆Mal), 4-(α-D-glucopyranosyl)-2-deoxy-α-D-glucopyranosyl (2-deoxyMal), 4-(2',3',4',6'-tetra-O-acetyl-β-D-galactopyranosyl)-6-O-acetyl-2,3-dideoxy-α-D-erythro-hex-2-enopyranosyl (FerrierAc₅Lac), 4-(β-D-galactopyranosyl)-2,3-dideoxy-α-D-erythro-hex-2-enopyranosyl (FerrierLac), 4-(2',3',4',6'-tetra-O-acetyl-α-D-glucopyranosyl)-6-O-acetyl-2,3-dideoxy-α-D-erythro-hex-2-enopyranosyl (FerrierAc₅Mal), 4-(α-D-glucopyranosyl)-2,3-dideoxy-α-D-erythro-hex-2-enopyranosyl (FerrierMal), 3,4-di-O-acetyl-2-deoxy-α-L-rhamnosyl (2-deoxyAc₂Rha), 2-deoxy-α-L-rhamnosyl (2-deoxyRha), 4-O-acetyl-2,3-dideoxy-3-brom-α-L-rhamnosyl (2-deoxyAcBrRha), 4-O-acetyl-2,3,6-trideoxy-α-L-erythro-hex-2-enopyranosyl (FerrierAcRha), 2,3,6-trideoxy-α-L-erythro-hex-2-enopyranosyl (FerrierRha) and hydrogen;
$R^{2a}$ is selected from the group comprising 2-deoxy-α-D-galactopyranosyl (2-deoxyGal), 3,4,6-tri-O-acetyl-2-deoxy-α-D-galactopyranosyl (2-deoxyAc₃Gal), 2-deoxy-α-D-glucopyranosyl (2-deoxyGlc), 3,4,6-tri-O-acetyl-2-deoxy-α-D-glucopyranosyl (2-deoxyAc₃Glc), 4,6-di-O-acetyl-3-brom-2,3-dideoxy-α-D-glucopyranosyl (2-deoxyBrAc₂Glc), 4-(2',3',4',6'-tetra-O-acetyl-β-D-galactopyranosyl)-3,6-di-O-acetyl-2-deoxy-α-D-glucopyranosyl (2-deoxyAc₆Lac), 4-(β-D-galactopyranosyl)-2-deoxy-α-D-glucopyranosyl (2-deoxyLac), 4-(2',3',4',6'-tetra-O-acetyl-α-D-glucopyranosyl)-3,6-di-O-acetyl-2-deoxy-α-D-glucopyranosyl (2-deoxyAc₆Mal), 4-(α-D-glucopyranosyl)-2-deoxy-α-D-glucopyranosyl (2-deoxyMal), 4-(2',3',4',6'-tetra-O-acetyl-β-D-galactopyranosyl)-6-O-acetyl-2,3-dideoxy-α-D-erythro-hex-2-enopyranosyl (FerrierAc₅Lac), 4-(β-D-galactopyranosyl)-2,3-dideoxy-α-D-erythro-hex-2-enopyranosyl (FerrierLac), 4-(2',3',4',6'-tetra-O-acetyl-α-D-glucopyranosyl)-6-O-acetyl-2,3-dideoxy-α-D-erythro-hex-2-enopyranosyl (FerrierAc₅Mal), 4-(α-D-glucopyranosyl)-2,3-dideoxy-α-D-erythro-hex-2-enopyranosyl (FerrierMal), 3,4-di-O-acetyl-2-deoxy-α-L-rhamnosyl (2-deoxyAc₂Rha), 2-deoxy-α-L-rhamnosyl (2-deoxyRha), 4-O-acetyl-2,3-dideoxy-3-brom-α-L-rhamnosyl (2-deoxyAcBrRha), 4-O-acetyl-2,3,6-trideoxy-α-L-erythro-hex-2-enopyranosyl (FerrierAcRha), 2,3,6-trideoxy-α-L-erythro-hex-2-enopyranosyl (FerrierRha) and hydrogen;

provided that
when "a" is a single bond (s), "b" is a double bond (d), and when "b" is a single bond (s), "a" is a double bond (d);
when "a" is a single bond, $R^4$ is $CH_3$, and when "a" is a double bond, $R^4$ is $CH_2$;
when $X^2$ is C=O and $X^3$ is $CH_2$, "a" is a single bond (s) and "b" is a double bond (d);
when $X^2$ is C=O and $X^3$ is C=O, "a" is a single bond (s) and "b" is a double bond (d);
at least one of $X^1$ and $R^2$ comprises 2-deoxy glycosyl
when $R^2$ is $COO(CH_2)_nCH_3$, wherein n=0 or 1, $R^1$ is not 2-deoxy-α-D-galactopyranosyl (2-deoxyGal), 3,4,6-tri-O-acetyl-2-deoxy-α-D-galactopyranosyl (2-deoxyAc₃Gal), 2-deoxy-α-D-glucopyranosyl (2-deoxyGlc), 3,4,6-tri-O-acetyl-2-deoxy-α-D-glucopyranosyl (2-deoxyAc₃Glc).

Another object of the invention is a pharmaceutical composition, which contains at least one compound of general formula Ia and a pharmaceutically acceptable carrier.

Suitable ways of administration are generally oral, rectal, vasal local (comprising ocular, buccal and sublingual), vaginal and parenteral (comprising subcutaneous, intramuscular, intravitreous, intravenous, intradermal, intrathecal and epidural). The preferred way of administration depends on the condition of the patient, the treatment regime and the location of the disease, among other considerations known to the physician.

The therapeutical preparation contains preferably 0.1 to 95% of the active substance, while single doses contain preferably 20 to 90% of the active substance and the doses that are not destined to single-dose application contain preferably 0.1 to 20% of the active substance. Single dose forms are e.g., coated tablets, tablets, ampoules, injections, vials, suppositories or capsules. Other application forms are e.g., ointments, creams, tinctures, sprays, dispersions etc. The pharmaceutical composition of the present invention are prepared by conventional methods known to those skilled in the art, e.g., by mixing, dissolving or lyofilization.

The pharmaceutically acceptable carriers may be the substances commonly used for this purpose, such as solvents, fillers, buffers, stabilizers, ointment bases, solid carriers, such as saccharides, starches, silicates, biopolymers etc.

In a preferred embodiment of the pharmaceutical composition according to the invention, the compound of general formula can be in the form of an inclusion compound with cyclodextrin and other pharmaceutically acceptable additives (according to the process described in WO 2008/037226). This formulation may be used particularly in the form of a water-based solution or in the form of a lyofilized powder, particularly for oral or intravenous administration.

EXAMPLES OF CARRYING OUT THE INVENTION

Melting points were measured on Kofler block and are uncorrected.

Varian$^{UNITY}$INOVA-400 ($^1$H at 399.95 MHz, $^{13}$C at 100.58 MHz) was used for measuring NMR spectra in CDCl$_3$ solution, in case of deacetylated 2-deoxy glycosides with an addition of CD$_3$OD. Chemical shifts in $^{13}$C NMR spectra were referenced to $\delta$(CDCl$_3$)=77.00 ppm. Signal multiplicity in $^{13}$C NMR spectra was determined from DEPT spectra. Chemical shifts were rounded to two decimal places, interaction constant in Hz units to one decimal place.

Specific optical rotations were measure in chloroform on the polarimeter AUTOMATIC POLARIMETER, Autopol III (Rudolph research, Flanders, N.J.).

The course of the reactions and the purity of the samplex were observed by TLC (thin-layer chromatography) on the foils Kieselgel 60 F$_{254}$ (Merck). Detection of TLC foils was carried out first by UV rays (model UVS-54; 254 nm) and then by spraying with 10% sulphuric acid and heating to 110-200° C.

The used HPLC (high-performance liquid chromatography) system had the following construction: high-pressure pump Gilson (model 321-322), preparative HPLC column (50×250 mm, sorbent Biospher Si 120, 7 μm), refractometric detector IOTA 2 (Precision Instruments), connected through RS-232 with the PC programme Chromulan 1.20 and automatic fraction collector Gilson (model 206).

Overview of the notation of compounds of general formula I used herein:

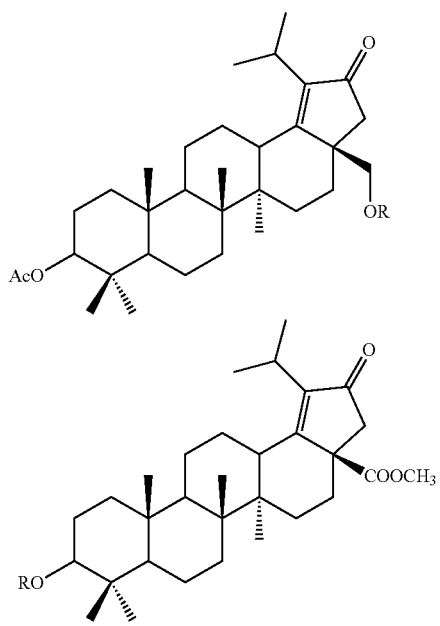

1a R=3,4,6-tri-O-acetyl-2-deoxy-α-D-galactopyranosyl
1b R=3,4,6-tri-O-acetyl-2-deoxy-α-D-glucopyranosyl
1c R=4,6-di-O-acetyl-3-brom-2,3-dideoxy-α-D-glucopyranosyl
4 R=H
2a R=H
2b R=3,4,6-tri-O-acetyl-2-deoxy-α-D-galactopyranosyl
2c R=4,6-di-O-acetyl-3-brom-2-deoxy-α-D-glucopyranosyl
2c R=3,4,6-tri-O-acetyl-2,3-dideoxy-α-D-glucopyranosyl
3a R=2-deoxy-α-D-galactopyranosyl
3b R=2-deoxy-α-D-glucopyranosyl

Example 1

Preparation of Acetylated Galactoside 1a

Into a solution of hydroxyketone 4 (110 mg; 0.2 mmol) in dry acetonitrile (6 ml), acetate of D-galactal (0.25 mmol), molecular sieve 4 A (100 mg), lithium bromide (150 mg) and Amberlyst® 15 in H$^+$-cycle (180 mg) were added. The reaction mixture was stirred at room temperature for 12 hours. The course of the reaction was observed by TLC. The reaction mixture was then filtered over a kieselguhr layer and the column was washed with ethyl acetate. The filtrate was diluted with water, extracted with ethyl acetate and the organic phase was evaporated at a rotary vacuum evaporator (RVO). The evaporation residue was dissolved in chloroform and the solution was poured over a short column of silica gel (elution by ethyl acetate). The eluate was evaporated at an RVO. The crude product was then separated by HPLC, with mixture of ethyl acetate and hexane in the volume ration of 5:4 as the mobile phase. Lyofilization from t-BuOH gave white lyofilisate 1a (33 mg; 20%). [α]$_D$+23.3×10$^{-1}$ deg cm$^2$ g$^{-1}$ (c=0.41 g/100 ml)

$^{13}$C NMR: 15.88 (C27), 16.50 (C24), 16.73 (C26), 16.83 (C25), 18.08 (C6), 20.00 (C29), 20.52 (C30), 20.71 (AcO: CH$_3$ 4), 20.76 (AcO: CH$_3$ 3), 20.83 (AcO: CH$_3$ 2), 21.28 (C11), 21.29 (AcO: CH$_3$ 1), 23.58 (C2), 25.14 (C20), 27.36 (C15), 27.77 (C12), 27.88 (C23), 29.96 (C2'), 32.03 (C16), 34.74 (C7), 37.09 (C10), 37.72 (C4), 38.52 (C1), 41.32 (C8), 42.74 (C13), 45.52 (C14), 46.06 (C17), 48.14 (C22), 50.90 (C9), 55.37 (C5), 62.14 (C6'), 65.35 (C3'), 65.98 (C4'), 66.82 (C5'), 70.81 (C28), 80.66 (C3), 97.77 (C1'), 146.35 (C19), 169.96 (AcO: C=O 4), 170.23 (AcO: C=O 3), 170.42 (AcO: C=O 2), 170.98 (C18), 172.48 (AcO: C=O 1), 208.24 (C21)

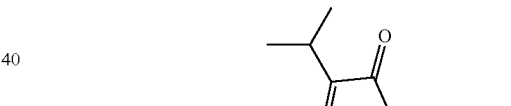

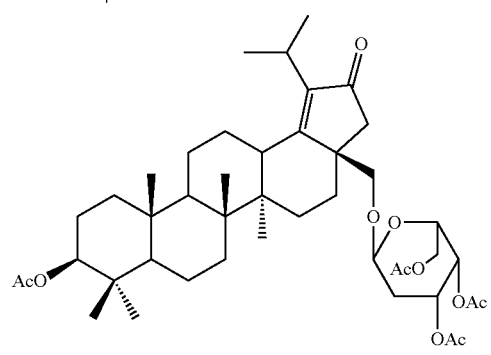

1a

Preparation of 2-deoxygalactoside 1a a: tri-O-acetylgalactal, LiBr, Amberlyst 15, Molecular Sieve 4 A/CH$_3$CN

Example 2

Preparation of Acetylated Glucosides 1b and 1c

Into a solution of hydroxyketone 4 (1.00 g; 2 mmol) in benzonitrile (60 ml), 3,4,6-tri-O-acetyl-D-glucal (640 mg, 2.4 mmol), molecular sieve 4 A (1.00 g), lithium bromide (1.46 g) and Amberlyst® 15 (1.80 g) were added. The reaction mixture was stirred at room temperature for 12 hours. The course of the reaction was observed by TLC. The reaction mixture was then filtered through kieselguhr, the filtration cake was washed with ethyl acetate. The filtrate was shaken with water (2×30 ml). The organic phase was mixed with water and the emulsion was evaporated at an RVO to the volume of the organic phase ca 10 ml. The emulsion was separated in a separation funnel. The reaction mixture was then separated by HPLC, with a mixture of ethyl acetate and hexane in the volume ration of 11:8 as the mobile phase. Lyofilization gave white 2-deoxy-3,4,6-tri-O-acetyl-α-D-glucoside 1b (172 mg; 11%) and 2,3-dideoxy-4,6-di-O-acetyl-3-bromo-α-D-glucoside 1c (203 mg; 13%). 1b: $[\alpha]_D$+11.8×10$^{-1}$ deg cm$^2$ g$^{-1}$ (c=0.41 g/100 ml); 1c: $[\alpha]_D$−3.7×10$^{-1}$ deg cm$^2$ g$^{-1}$ (c=0.43 g/100 ml)

$^{13}$C NMR 1b: 15.76 (C27), 16.27 (C24), 16.62 (C26), 16.62 (C25), 17.89 (C6), 19.74 (C29), 20.23 (C30), 20.48 (AcO: CH$_3$ 4), 20.54 (AcO: CH$_3$ 3), 20.67 (AcO: CH$_3$ 2), 21.07 (AcO: CH$_3$ 1), 21.09 (C11) 23.37 (C2), 24.93 (C20), 27.16 (C15), 27.55 (C12), 27.67 (C23), 31.91 (C16), 34.28 (C2'), 34.28 (C7), 36.92 (C10), 37.57 (C4), 38.32 (C1), 41.18 (C8), 42.63 (C13), 45.43 (C14), 45.87 (C17), 47.91 (C22), 50.72 (C9), 55.18 (C5), 62.06 (C6'), 68.00 (C3'), 68.79 (C4'), 68.99 (C5'), 70.76 (C28), 80.87 (C3), 97.18 (C1'), 146.16 (C19), 170.09 (AcO: C═O 4), 170.22 (AcO: C═O 3), 170.95 (AcO: C═O 2), 171.46 (C18), 173.53 (AcO: C═O 1), 209.05 (C21)

$^{13}$C NMR 1c: 15.80 (C27), 16.34 (C24), 16.66 (C26), 16.69 (C25), 17.92 (C6), 19.74 (C29), 20.41 (C30), 20.56 (AcO: CH$_3$ 3), 20.61 (AcO: CH$_3$ 2), 21.14 (AcO: CH$_3$ 1), 21.12 (C11) 23.41 (C2), 24.99 (C20), 27.23 (C15), 27.62 (C12), 27.72 (C23), 32.13 (C16), 34.60 (C7), 36.96 (C10), 37.61 (C4), 38.36 (C1), 40.33 (C2'), 41.20 (C8), 42.55 (C13), 45.28 (C3'), 45.42 (C14), 45.87 (C17), 48.01 (C22), 50.74 (C9), 55.22 (C5), 62.37 (C6'), 69.61 (C4'), 70.66 (C28), 71.11 (C5'), 80.84 (C3), 97.30 (C1'), 146.32 (C19), 169.72 (AcO: C═O 3), 170.95 (AcO: C═O 2), 171.41 (C18), 172.99 (AcO: C═O 1), 208.87 (C21)

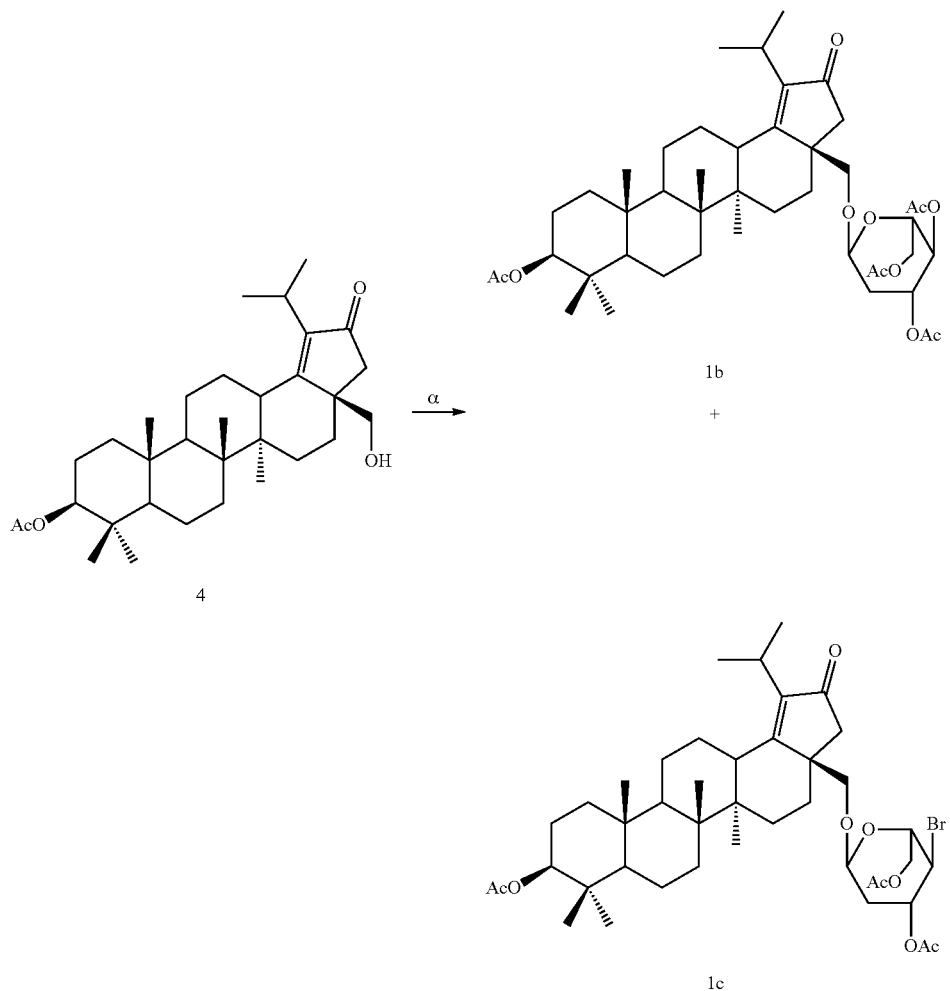

Preparation of 2-deoxyglucosides 1b a 1c a: tri-O-acetylglucal, LiBr, Amberlyst 15, Molecular Sieve 4 A/CH₃CN

Example 3

Preparation of Acetylated Galactoside 2b

Into a solution of hydroxymethyl ester 2a (500 mg; 1 mmol) in dry acetonitrile (30 ml), acetate of D-galactal (1.2 mmol), molecular sieve 4 A (500 mg), lithium bromide (730 mg) and Amberlyst® 15 in H⁺-cycle (900 mg) were added. The reaction mixture was stirred at room temperature for 12 hours. The course of the reaction was observed by TLC. The reaction mixture was then filtered through a kieselguhr layer and the column was washed with ethyl acetate. The filtrate was diluted with water, extracted with ethyl acetate and the organic phase was evaporated at an RVO. The evaporation residue was dissolved in chloroform and the solution was poured over a short column of silica gel (elution by ethyl acetate). The eluate was evaporated at an RVO. The crude product was then separated by HPLC. White lyofilisate (t-BuOH) 2b was obtained (360 mg; 47%). $[\alpha]_D$+38.9×10⁻¹ deg cm² g⁻¹ (c=0.52 g/100 ml)

¹³C NMR: 15.89 (C27), 16.31 (C24), 16.64 (C26), 16.76 (C25), 18.14 (C6), 19.98 (C29), 20.10 (C30), 20.73 (AcO: CH₃ 3), 20.77 (AcO: CH₃ 2), 20.90 (AcO: CH₃ 1), 21.19 (C11), 21.96 (C2), 25.08 (C20), 27.64 (C12), 28.50 (C23), 29.08 (C15), 30.73 (C2'), 33.66 (C16), 34.89 (C7), 37.12 (C10), 38.40 (C4), 38.51 (C1), 41.27 (C8), 45.15 (C13), 45.16 (C14), 47.60 (C22), 51.11 (C9), 52.48 (COOCH₃), 53.05 (C17), 55.74 (C5), 62.47 (C6'), 66.39 (C3'), 66.75 (C4'), 67.02 (C5'), 82.63 (C3), 93.64 (C1'), 145.66 (C19), 170.10 (AcO: C=O 3), 170.33 (AcO: C=O 2), 170.43 (AcO: C=O 1), 171.83 (C18), 174.83 (C28), 207.29 (C21)

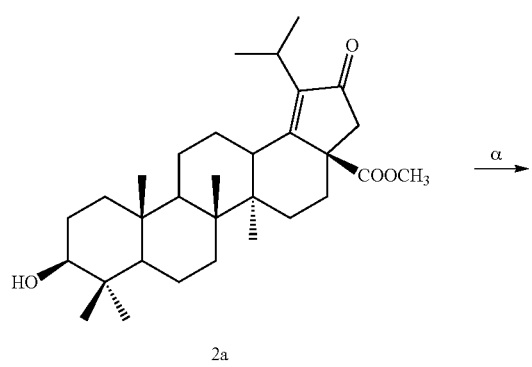

2a

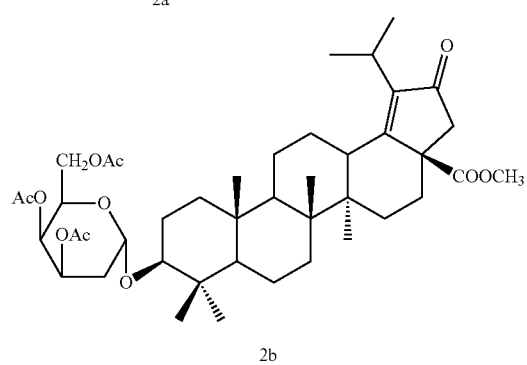

2b

Preparation of 2-deoxygalactoside 2b a: tri-O-acetylgalactal, LiBr, Amberlyst 15, Molecular Sieve 4 A/CH₃CN

Example 4

Preparation of Free Galactoside 3a

Acetylated 2-deoxy glycoside 2b (200 mg; 0.26 mmol) was dissolved in five-fold excess (by weight) of dry methanol and catalytic amount of sodium (5 mg) was added to the solution. The course of the reaction was observed by reverse TLC. The reaction mixture was neutralized by acetic acid and evaporated at an RVO. Water was added to the evaporation residue and the formed precipitate of the product was filtered. The filtration cake was washed with water. White crystalline 2-deoxy galactoside 3a was obtained (161 mg; 97%) $[\alpha]_D$+ 17.2×10⁻¹ deg cm² g⁻¹ (c=0.51 g/100 ml)

¹³C NMR: 15.76 (C27), 16.13 (C24), 16.47 (C26), 16.61 (C25), 17.99 (C6), 19.74 (C29), 19.86 (C30), 21.01 (C11), 21.57 (C2), 24.87 (C20), 27.47 (C12), 28.22 (C23), 28.90 (C15), 32.94 (C2'), 33.49 (C16), 36.98 (C10), 37.71 (C7), 38.25 (C4), 38.29 (C1), 41.14 (C8), 45.12 (C14), 45.16 (C13), 47.41 (C22), 50.89 (C9), 52.41 (COOCH₃), 53.01 (C17), 55.41 (C5), 62.45 (C6'), 65.34 (C3'), 68.82 (C4'), 69.85 (C5'), 81.42 (C3), 93.30 (C1'), 145.54 (C19), 172.66 (C18), 174.88 (C28), 207.96 (C21)

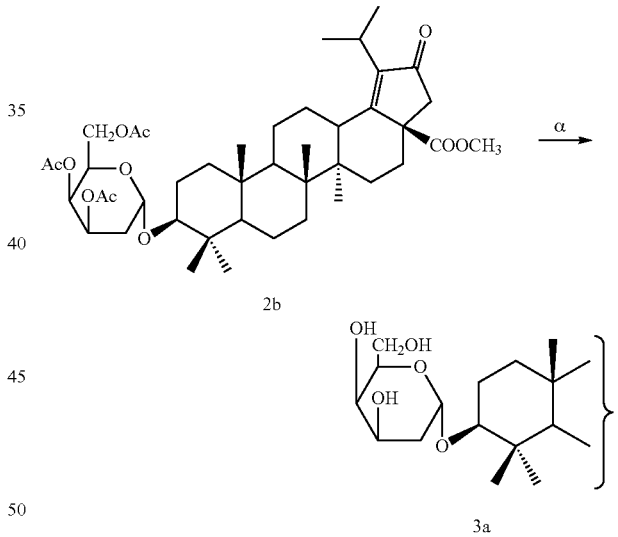

2b

3a

Deprotection of acetylated 2-deoxygalactoside 2b: a

CH₃ONa/CH₃OH

Example 5

Preparation of Free Glucoside 3b

Into a solution of hydroxymethyl ester 2a (500 mg; 1 mmol) in dry acetonitrile (30 ml), acetate of D-galactal (1.2 mmol), molecular sieve 4 A (500 mg), lithium bromide (730 mg) and Amberlyst® 15 in H⁺-cycle (900 mg) were added. The reaction mixture was stirred at room temperature for 12 hours. The course of the reaction was observed by TLC. The reaction mixture was then filtered through a layer of kieselguhr and the column was washed with ethyl acetate. The filtrate was diluted with water, extracted with ethyl acetate and the organic phase was evaporated at an RVO. The evaporation residue was dissolved in chloroform and the solution was poured over a short column of silica gel (elution by ethyl acetate). The eluate was evaporated at an RVO. The crude product was then separated by HPLC. Thus, 2,3-dideoxy-3,4-di-O-acetyl-3-bromo-α-D-glucoside 2c in the form of white crystals (245 mg; 31%) and 2-deoxy-3,4,6-tri-O-acetyl-α-D-glucoside 2d (101 mg; 13%) were obtained. Acetylated 2-deoxy glucoside 2d (60 mg; 0.08 mmol) was dissolved in five-fold excess (by weight) of dry methanol and catalytic amount of sodium (5 mg) was added into the solution. The reaction was carried out at the temperature of 45° C. The course of the reaction was observed by reverse TLC. The reaction mixture was neutralized by acetic acid and evaporated at an RVO. Water was added to the evaporation residue and the formed precipitate of the product was filtered. The filtration cake was washed with water. White crystalline 2-deoxy glucoside 3b (39 mg; 74%) was obtained. $[\alpha]_D$ 0.0× $10^{-1}$ deg cm$^2$ g$^{-1}$ (c=0.40 g/100 ml)

$^{13}$C NMR: 15.74 (C27), 16.09 (C24), 16.45 (C26), 16.59 (C25), 17.97 (C6), 19.72 (C29), 19.84 (C30), 20.99 (C11), 21.57 (C2), 24.86 (C20), 27.46 (C12), 28.24 (C23), 28.89 (C15), 37.62 (C2'), 33.47 (C16), 36.96 (C10), 37.70 (C7), 38.21 (C4), 38.28 (C1), 41.13 (C8), 45.10 (C14), 45.16 (C13), 47.39 (C22), 50.88 (C9), 52.41 (COOCH$_3$), 53.00 (C17), 55.43 (C5), 62.69 (C6'), 68.61 (C3'), 71.92 (C4'), 72.14 (C5'), 81.40 (C3), 93.13 (C1'), 145.51 (C19), 172.71 (C18), 174.87 (C28), 207.99 (C21)

Example 6

Antitumor Activity in Vitro

Cytotoxic MTT test on cell lines derived from normal tissues and tumors were used for assessing the antitumor activity of the novel compounds in vitro. We used namely the lines K562 (human myeloid leukemia), K562-tax (human myeloid leukemia resistant to taxol and overexpressing the protein of multiple drug resistance PgP), CEM (T-lymfoblastic leukemia), CEM-DNR-bulk (T-lymfoblastic leukemia resistant to doxorubicin, lacking the expression of the target gene for topoisomerase II alfa inhibitors and expressing the multiple drug resistance protein MRP1), line A549 (human lung adenocarcinoma), line HT-29 (human colorectal adenocarcinoma), MCF-7 (human breast adenocarcinoma, p53 wild type), HCT116 p53wt (human colorectal adenocarcinoma, wild-type p53), HCT116 p53mut (human colorectal adenocarcinoma with mutated p53), U87Mg (human glioblastoma). Expression characteristics, sensitivity profiles to classical antitumor drugs and methodology of the cytotoxic MTT test were repeatedly published (Nosková V. et al., Neoplasma 2002, Š arek J. et al., J. Med. Chem., 2003, Džubák P. et al., Bioorg. Med. Chem., 2006).

The MTT test was carried out according to the following procedure. The tested compound in six dilutions (final concentration of 250 μmol/l, another five concentrations were obtained by 4-fold, 16-fold, 64-fold, 256-fold and 1024-fold dilution of this solution) was added to tissue culture of cells in the cultivation plate wells. Each concentration was tested in doublet. The cell suspension was incubated in the environment containing the tested compound for 72 h at 37° C., in 5% $CO_2$ atmosphere and 100% humidity. MTT—[3-(4,5-dimethylthiazol-2-yl)-2,5-difenyl-2H-tetrazolium bromid]—was then added to each well and the incubation was continued for additional 4 h. The incubation was finished by an addition of sodium dodecansulphonate and the percentage of surviving cells was determined spectrophotometrically at 540 nm. The concentration lethal for 50% of the tumor cells—$IC_{50}$—was calculated from dose-response curves.

The results of testing are shown in Table 1. The tested compounds have shown cytotoxicity to a wide range of tumor lines of various histogenetic origin, which was slightly decreased in lines with drug resistance protein expression and comparable in cells bearing a mutated p53 gene.

TABLE 1

Antitumor activity of the compounds of general formula I:

| Compound | $IC_{50}$ [μmol/l] | | | | | | | | | |
|---|---|---|---|---|---|---|---|---|---|---|
| | CEM | MCF-7 | CEM-DNR-BULK | K562 | K562-tax | HT-29 | PC-3 | U87Mg | HCT116 p53 mut | HCT116 p53wt |
| 1a | 1.8 | 11.4 | 12.5 | 2.4 | 9.8 | 11.4 | 23.5 | 250 | 8.8 | 7.9 |
| 1b | 9.2 | 17.0 | 41.5 | 6.4 | 9.5 | 10.1 | 39.3 | 250 | 12.4 | 8.6 |
| 1c | 3.8 | 35.2 | 27.0 | 9.0 | 22.6 | 40.9 | 250 | 250 | 14.0 | 19.1 |
| 2b | 0.6 | 2.5 | 25.0 | 0.6 | 3.0 | 2.4 | 22.1 | 250 | 3.5 | 1.6 |
| 3a | 4.7 | 13.6 | 34.4 | 11.5 | 15.9 | 17.8 | 11.2 | 53.0 | 17.5 | 10.3 |
| 3b | 6.2 | 18.4 | 25.0 | 11.6 | 12.9 | 18.9 | 36.4 | 42.7 | 21.0 | 11.5 |

Example 7

Pharmaceutical Composition 2-hydroxypropyl-γ-cyclodextrin (7.00 g) was dissolved under vigorous stirring and at the temperature of 50° C. in a mixture of water (14.0 ml) and propylene glycol (6.0 ml). 2-deoxy galactoside 3a (1.00 g) is then added at once into the resulting colourless viscous solution and the mixture is vigorously stirred at the temperature of 50° C. Usually, 20 min is needed for complete dissolution. After complete dissolution of the triterpenoid, the resulting bright solution is cooled down to room temperature, filtered by an injection syringe filter (hydrophilic, pore size 0.22 μm) in order to be sterile and is placed to a refrigerator. The obtained solution can be stored in a freezer at −20 C for several months without any detectable decomposition. The thus prepared formulation can be used for oral or, after optionally adding a saline solution, for intravenous administration.

The invention claimed is:
1. Triterpenoid 2-deoxy glycosides of general formula I

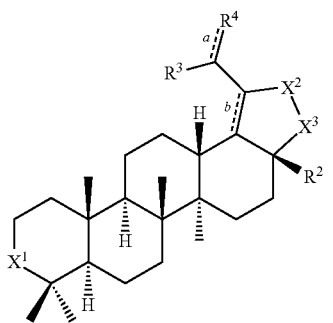

wherein:
each of "a" and "b" is a double or a single bond;
$R^2$ is selected from the group comprising COOH, $COOCH_2C_6H_5$, $COO(CH_2)_nCH_3$, wherein n=0-10, and $CH_2OR^{2a}$;
$R^3$ is $CH_3$ or CHO;
$R^4$ is $CH_3$ or $CH_2$;
$X^1$ is CHOW or C=O;
$X^2$ is C=O;
$X^3$ is $CH_2$ or C=O;
$R^1$ is selected from the group comprising hydrogen, acetyl, and 2-deoxy glycosyls selected from 2-deoxy-α-D-galactopyranosyl, 3,4,6-tri-O-acetyl-2-deoxy-α-D-galactopyranosyl, 2-deoxy-α-D-glucopyranosyl, 3,4,6-tri-O-acetyl-2-deoxy-α-D-glucopyranosyl, 4,6-di-O-acetyl-3-brom-2,3-dideoxy-α-D-glucopyranosyl, 4-(2',3',4',6'-tetra-O-acetyl-β-D-galactopyranosyl)-3,6-di-O-acetyl-2-deoxy-α-D-glucopyranosyl, 4-(β-D-galactopyranosyl)-2-deoxy-α-D-glucopyranosyl, 4-(2',3',4',6'-tetra-O-acetyl-α-D-glucopyranosyl)-3,6-di-O-acetyl-2-deoxy-α-D-glucopyranosyl, 4-(α-D-glucopyranosyl)-2-deoxy-α-D-glucopyranosyl, 4-(2',3',4',6'-tetra-O-acetyl-β-D-galactopyranosyl)-6-O-acetyl-2,3-dideoxy-α-D-erythro-hex-2-enopyranosyl, 4-(β-D-galactopyranosyl)-2,3-dideoxy-α-D-erythro-hex-2-enopyranosyl, 4-(2',3',4',6'-tetra-O-acetyl-α-D-glucopyranosyl)-6-O-acetyl-2,3-dideoxy-α-D-erythro-hex-2-enopyranosyl, 4-(α-D-glucopyranosyl)-2,3-dideoxy-α-D-erythro-hex-2-enopyranosyl, 3,4-di-O-acetyl-2-deoxy-α-L-rhamnosyl, 2-deoxy-α-L-rhamnosyl, 4-O-acetyl-2,3-dideoxy-3-brom-α-L-rhamnosyl, and 4-O-acetyl-2,3,6-trideoxy-α-L-erythro-hex-2-enopyranosyl, 2,3,6-trideoxy-α-L-erythro-hex-2-enopyranosyl;
$R^{2a}$ is selected from the group comprising hydrogen, and 2-deoxy glycosyls selected from 2-deoxy-α-D-galactopyranosyl, 3,4,6-tri-O-acetyl-2-deoxy-α-D-galactopyranosyl, 2-deoxy-α-D-glucopyranosyl, 3,4,6-tri-O-acetyl-2-deoxy-α-D-glucopyranosyl, 4,6-di-O-acetyl-3-brom-2,3-dideoxy-α-D-glucopyranosyl, 4-(2',3',4',6'-tetra-O-acetyl-β-D-galactopyranosyl)-3,6-di-O-acetyl-2-deoxy-α-D-glucopyranosyl, 4-(β-D-galactopyranosyl)-2-deoxy-α-D-glucopyranosyl, 4-(2',3',4',6'-tetra-O-acetyl-α-D-glucopyranosyl)-3,6-di-O-acetyl-2-deoxy-α-D-glucopyranosyl, 4-(2',3',4',6'-tetra-O-acetyl-β-D-galactopyranosyl)-6-O-acetyl-2,3-dideoxy-α-D-erythro-hex-2-enopyranosyl, 4-(β-D-galactopyranosyl)-2,3-dideoxy-α-D-erythro-hex-2-enopyranosyl, 4-(2',3',4',6'-tetra-O-acetyl-α-D-glucopyranosyl)-6-O-acetyl-2,3-dideoxy-α-D-erythro-hex-2-enopyranosyl, 4-(α-D-glucopyranosyl)-2,3-dideoxy-α-D-erythro-hex-2-enopyranosyl, 3,4-di-O-acetyl-2-deoxy-α-L-rhamnosyl, 2-deoxy-α-L-rhamnosyl, 4-O-acetyl-2,3-dideoxy-3-brom-α-L-rhamnosyl, and 4-O-acetyl-2,3,6-trideoxy-α-L-erythro-hex-2-enopyranosyl, 2,3,6-trideoxy-α-L-erythro-hex-2-enopyranosyl;

provided that:
when "a" is a single bond, "b" is a double bond, and when "b" is a single bond, "a" is a double bond;
when "a" is a single bond, $R^4$ is $CH_3$, and when "a" is a double bond, $R^4$ is $CH_2$;
when $X^2$ is C=O and $X^3$ is $CH_2$, "a" is a single bond and "b" is a double bond;
when $X^2$ is C=O and $X^3$ is C=O, "a" is a single bond and "b" is a double bond;
at least one of $X^1$ and $R^2$ comprises 2-deoxy glycosyl;
for use as medicaments.

2. A method of preparation of the triterpenoid 2-deoxy glycosides of general formula I, according to claim 1, comprising the steps of:
a) reaction of triterpenic hydroxy derivative of general formula II

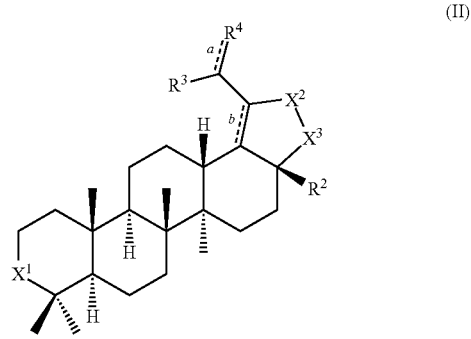

wherein:
each of "a" and "b" is a double or a single bond;
$R^2$ is $COO(CH_2)_nCH_3$, wherein n=0-10, $COOCH_2C_6H_5$, COOH or $CH_2OH$;
$R^3$ is $CH_3$ or CHO;
$R^4$ is $CH_3$ or $CH_2$;
$X^1$ is CHOW or C=O;
$X^2$ is C=O;
$X^3$ is $CH_2$ or C=O;
$R^1$ is acetyl (Ac) or hydrogen;
provided that:
when "a" is a single bond, "b" is a double bond, and when "b" is a single bond, "a" is a double bond;
when "a" is a single bond, $R^4$ is $CH_3$, and when "a" is a double bond, $R^4$ is $CH_2$;
when $X^2$ is C=O and $X^3$ is $CH_2$, "a" is a single bond and "b" is a double bond;
when $X^2$ is C=O and $X^3$ is C=O, "a" is a single bond and "b" is a double bond;

when $R^2$ is not $CH_2OH$, $X^1$ is $CHOR^1$ and $R^1$ is hydrogen,
    with acetylated glycal in dry nitrile solvent, in the presence of katex in $H^+$ cycle, halogenide and molecular sieve, yielding acetylated triterpenoid 2-deoxy glycoside;
b) optional deacetylation of the acetylated triterpenoid 2-deoxy glycoside obtained in step a) by Zemplén deacetylation by treatment with sodium alcoholate in dry alcohol.

3. The method according to claim 2, wherein in step a), a solvent selected from the group comprising acetonitrile and benzonitrile is used as the dry nitrile solvent, lithium bromide is used as the halogenide and molecular sieve 4 A is used as the molecular sieve, and in step b), sodium methanolate is used as the sodium alcoholate and methanol or a mixture of methanol and ethanol is used as the dry alcohol.

4. Triterpenoid 2-deoxy glycosides of general formula Ia

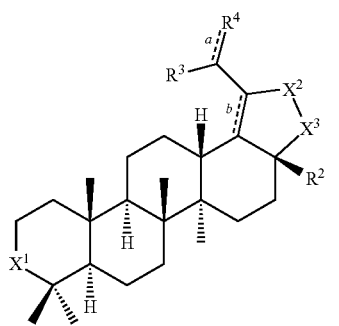

(Ia)

wherein:
each of "a" and "b" is a double or a single bond;
$R^2$ is selected from the group comprising COOH, $COOCH_2C_6H_5$, $COO(CH_2)_NCH_3$, wherein n=0-10, and $CH_2OR^{2a}$;
$R^3$ is $CH_3$ or CHO;
$R^4$ is $CH_3$ or $CH_2$;
$X^1$ is CHOW or C=O;
$X^2$ is C=O;
$X^3$ is $CH_2$ or C=O;
$R^1$ is selected from the group comprising hydrogen, acetyl, and 2-deoxy glycosyls selected from 2-deoxy-α-D-galactopyranosyl, 3,4,6-tri-O-acetyl-2-deoxy-α-D-galactopyranosyl, 2-deoxy-α-D-glucopyranosyl, 3,4,6-tri-O-acetyl-2-deoxy-α-D-glucopyranosyl, 4,6-di-O-acetyl-3-brom-2,3-dideoxy-α-D-glucopyranosyl, 4-(2',3',4',6'-tetra-O-acetyl-β-D-galactopyranosyl)-3,6-di-O-acetyl-2-deoxy-α-D-glucopyranosyl, 4-(β-D-galactopyranosyl)-2-deoxy-α-D-glucopyranosyl, 4-(2',3',4',6'-tetra-O-acetyl-α-D-glucopyranosyl)-3,6-di-O-acetyl-2-deoxy-α-D-glucopyranosyl, 4-(α-D-glucopyranosyl)-2-deoxy-α-D-glucopyranosyl, 4-(2',3',4',6'-tetra-O-acetyl-β-D-galactopyranosyl)-6-O-acetyl-2,3-dideoxy-α-D-erythro-hex-2-enopyranosyl, 4-(β-D-galactopyranosyl)-2,3-dideoxy-α-D-erythro-hex-2-enopyranosyl, 4-(2',3',4',6'-tetra-O-acetyl-α-D-glucopyranosyl)-6-O-acetyl-2,3-dideoxy-α-D-erythro-hex-2-enopyranosyl, 4-(α-D-glucopyranosyl)-2,3-dideoxy-α-D-erythro-hex-2-enopyranosyl, 3,4-di-O-acetyl-2-deoxy-α-L-rhamnosyl, 2-deoxy-α-L-rhamnosyl, 4-O-acetyl-2,3-dideoxy-3-brom-α-L-rhamnosyl, and 4-O-acetyl-2,3,6-trideoxy-α-L-erythro-hex-2-enopyranosyl, 2,3,6-trideoxy-α-L-erythro-hex-2-enopyranosyl;

$R^{2a}$ is selected from the group comprising hydrogen, and 2-deoxy glycosyls selected from 2-deoxy-α-D-galactopyranosyl, 3,4,6-tri-O-acetyl-2-deoxy-α-D-galactopyranosyl, 2-deoxy-α-D-glucopyranosyl, 3,4,6-tri-O-acetyl-2-deoxy-α-D-glucopyranosyl, 4,6-di-O-acetyl-3-brom-2,3-dideoxy-α-D-glucopyranosyl, 4-(2',3',4',6'-tetra-O-acetyl-β-D-galactopyranosyl)-3,6-di-O-acetyl-2-deoxy-α-D-glucopyranosyl, 4-(β-D-galactopyranosyl)-2-deoxy-α-D-glucopyranosyl, 4-(2',3',4',6'-tetra-O-acetyl-α-D-glucopyranosyl)-3, 6-di-O-acetyl-2-deoxy-α-D-glucopyranosyl, 4-(α-D-glucopyranosyl)-2-deoxy-α-D-glucopyranosyl, 4-(2',3',4',6'-tetra-O-acetyl-β-D-galactopyranosyl)-6-O-acetyl-2,3-dideoxy-α-D-erythro-hex-2-enopyranosyl, 4-(β-D-galactopyranosyl)-2,3-dideoxy-α-D-erythro-hex-2-enopyranosyl, 4-(2',3',4',6'-tetra-O-acetyl-α-D-glucopyranosyl)-6-O-acetyl-2,3-dideoxy-α-D-erythro-hex-2-enopyranosyl, 4-(α-D-glucopyranosyl)-2,3-dideoxy-α-D-erythro-hex-2-enopyranosyl, 3,4-di-O-acetyl-2-deoxy-α-L-rhamnosyl, 2-deoxy-α-L-rhamnosyl, 4-O-acetyl-2,3-dideoxy-3-brom-α-L-rhamnosyl, and 4-O-acetyl-2,3,6-trideoxy-α-L-erythro-hex-2-enopyranosyl, 2,3,6-trideoxy-α-L-erythro-hex-2-enopyranosyl;

provided that:
when "a" is a single bond, "b" is a double bond, and when "b" is a single bond, "a" is a double bond;
when "a" is a single bond, $R^4$ is $CH_3$, and when "a" is a double bond, $R^4$ is $CH_2$;
when $X^2$ is C=O and $X^3$ is $CH_2$, "a" is a single bond and "b" is a double bond;
when $X^2$ is C=O and $X^3$ is C=O, "a" is a single bond and "b" is a double bond;
at least one of $X^1$ and $R^2$ comprises 2-deoxy glycosyl
when $R^2$ is $COO(CH_2)_nCH_3$, wherein n=0 or 1, $R^1$ is not 2-deoxy-α-D-galactopyranosyl, 3,4,6-tri-O-acetyl-2-deoxy-α-D-galactopyranosyl, 2-deoxy-α-D-glucopyranosyl, 3,4,6-tri-O-acetyl-2-deoxy-α-D-glucopyranosyl.

5. A pharmaceutical composition comprising at least one compound of general formula Ia according to claim 4 and a pharmaceutically acceptable carrier.

* * * * *